(12) United States Patent
Minosawa et al.

(10) Patent No.: US 7,824,342 B2
(45) Date of Patent: Nov. 2, 2010

(54) TISSUE CUTTING DEVICE

(75) Inventors: Ryo Minosawa, Tsukui-gun (JP); Koji Shimomura, Tokyo (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 11/346,711

(22) Filed: Feb. 3, 2006

(65) Prior Publication Data

US 2007/0185511 A1     Aug. 9, 2007

(51) Int. Cl.
*A61B 10/00* (2006.01)
*A61B 17/24* (2006.01)
*A61B 17/26* (2006.01)

(52) U.S. Cl. .............. 600/564; 600/562; 600/569; 606/113

(58) Field of Classification Search .......... 600/562, 600/564, 566–569; 606/113
See application file for complete search history.

(56) References Cited

U.S. PATENT DOCUMENTS

| | | | | |
|---|---|---|---|---|
| 2,767,703 A * | 10/1956 | Nieburgs | ........... | 600/562 |
| 3,495,586 A * | 2/1970 | Regenbogen | ........... | 600/101 |
| 3,910,279 A | 10/1975 | Okada et al. | | |
| 5,098,440 A * | 3/1992 | Hillstead | ........... | 606/108 |
| 5,320,110 A * | 6/1994 | Wang | ........... | 600/566 |
| 5,643,282 A * | 7/1997 | Kieturakis | ........... | 606/114 |
| 5,683,384 A * | 11/1997 | Gough et al. | ........... | 606/41 |
| 6,123,665 A * | 9/2000 | Kawano | ........... | 600/104 |
| 6,344,026 B1 | 2/2002 | Burbank et al. | | |
| 6,517,498 B1 * | 2/2003 | Burbank et al. | ........... | 600/564 |
| 6,676,658 B2 * | 1/2004 | Burbank et al. | ........... | 606/45 |
| 6,699,206 B2 * | 3/2004 | Burbank et al. | ........... | 600/567 |
| 6,863,676 B2 * | 3/2005 | Lee et al. | ........... | 606/159 |
| 7,101,378 B2 * | 9/2006 | Salameh et al. | ........... | 606/113 |
| 7,192,430 B2 * | 3/2007 | Truckai et al. | ........... | 606/46 |

(Continued)

FOREIGN PATENT DOCUMENTS

DE     24 29 462     1/1975

(Continued)

OTHER PUBLICATIONS

Extended European Search Report dated Jul. 28, 2009 in corresponding European Patent Application No. EP 07 00 2109 (English language).

(Continued)

*Primary Examiner*—Max Hindenburg
*Assistant Examiner*—Sean P Dougherty
(74) *Attorney, Agent, or Firm*—Ostrolenk Faber LLP

(57) ABSTRACT

A tissue cutting device includes an insertion section which is inserted inside a specimen and extends from a distal end to a proximal end, openings which are formed in a distal end side of the insertion section inserted into the specimen, tissue cutting members which pass through the openings, extend such as to protrude in a direction intersecting the axial line of the length direction from the distal end of the insertion section to the proximal end, and are drawn into the insertion section from the same openings after forming a loop which tissue can be inserted into, a control member which is connected to the tissue cutting members, and a controller for controlling the control member; tissue passed through the loops being cut by controlling the control member and drawing the tissue cutting members from the openings into the insertion section.

17 Claims, 16 Drawing Sheets

U.S. PATENT DOCUMENTS

| | | | |
|---|---|---|---|
| 7,229,418 B2 * | 6/2007 | Burbank et al. | 600/564 |
| 7,303,531 B2 * | 12/2007 | Lee et al. | 600/564 |
| 7,322,939 B2 * | 1/2008 | Burbank et al. | 600/564 |
| 7,357,801 B2 * | 4/2008 | Burbank et al. | 606/45 |
| 7,534,242 B2 * | 5/2009 | Buehlmann et al. | 606/41 |
| 7,601,125 B1 * | 10/2009 | Kai | 600/564 |
| 2004/0087872 A1 * | 5/2004 | Anderson et al. | 600/564 |
| 2004/0267156 A1 * | 12/2004 | Turovskiy et al. | 600/564 |
| 2005/0004471 A1 * | 1/2005 | Hogendijk et al. | 600/463 |
| 2006/0149295 A1 * | 7/2006 | Fleming, III | 606/113 |

FOREIGN PATENT DOCUMENTS

| | | |
|---|---|---|
| JP | 08-336543 | 12/1996 |
| JP | 2000-051228 | 2/2000 |

OTHER PUBLICATIONS

Office Action issued by the Japanese Patent Office on May 25, 2010 in connection with corresponding Japanese Patent Application No. 2007-024595.

English translation of Japanese Office Action issued in connection with Japanese Patent Application No. 2007-024595 on May 25, 2010.

* cited by examiner

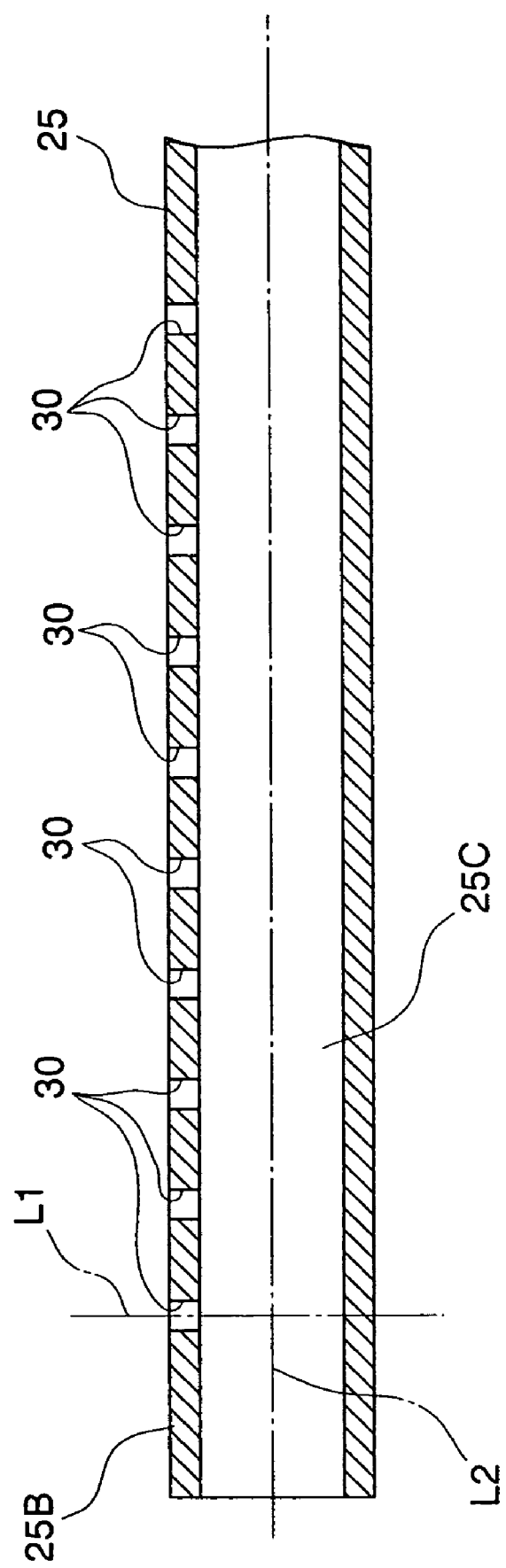

TISSUE CUTTING DEVICE

BACKGROUND OF THE INVENTION

1. Field of the Invention

The present invention relates to a tissue cutting device which cuts tissue in a specimen.

2. Description of Related Art

When performing a medical procedure (including observation, treatment, and so on; hereinafter the same) on human organs and the like, there is a conventional operation known as laparoscopic surgery in which, instead of widely cutting open an abdominal wall, a plurality of openings are made in the abdominal wall and rigid surgical instruments, such as a laparoscope or a forceps, are inserted into each of the openings to perform a surgical procedure. Since laparoscopic surgery can be performed by making small holes, it has advantages that it is only mildly intrusive and the patient makes a swift recovery.

When removing an organ such as a kidney during laparoscopic surgery, the abdominal wall is cut open to a size sufficient to extract the organ. If the organ is cut into small pieces of predetermined size inside the abdominal cavity before being removed to the outside, the abdominal wall need not be widely cut open. One instrument used in such medical procedures includes a cylindrical head main unit which is inserted into the body cavity, with a linear member led into two rows of insertion holes provided in the head main unit. The linear member passes inside the head main unit and is drawn outside from the first insertion hole. While forming a loop, the linear member is then drawn into the second insertion hole. The looped portion of the linear member forms a looped cutting portion for cutting an organ. Both ends of the linear member are secured to a control member. When cutting an organ, the organ is inserted inside the looped cutting portion before pulling the control member along the axial direction of the instrument. The looped cutting portion is drawn through the two insertion holes into the head main unit. The organ is then cut by reducing the loop diameter of the looped cutting portion.

SUMMARY OF THE INVENTION

A tissue cutting device according to a first aspect of the present invention comprises: an insertion section which is inserted inside a specimen and extends from a distal end to a proximal end; openings which are formed in a distal end side of the insertion section inserted into the specimen; tissue cutting members which pass through the openings, extend such as to protrude in a direction intersecting the axial line of the length direction from the distal end of the insertion section to the proximal end, and are drawn into the insertion section from the same openings after forming a loop which tissue can be inserted into; a control member which is connected to the tissue cutting members; and a controller for controlling the control member. Tissue passed into the loops is cut by controlling the control member and drawing the tissue cutting members from the openings into the insertion section.

A tissue cutting device according to a second aspect of the present invention comprises: an insertion section which can be inserted inside a specimen; tissue cutting members made from linear members and include looped portions which tissue can be passed into, the looped portions being extracted from the insertion section; openings which are formed in the insertion section, the tissue cutting members being able to be inserted through the openings, the openings enabling all the looped portions to be drawn inside the insertion section; and a controller which cuts the tissue passed into the looped portions by drawing the looped portions from the openings into the insertion section.

BRIEF DESCRIPTION OF THE DRAWINGS

FIG. 5 is a cross-sectional view taken along line C-C of FIG. 2;

DETAILED DESCRIPTION OF THE INVENTION

Figure 1:
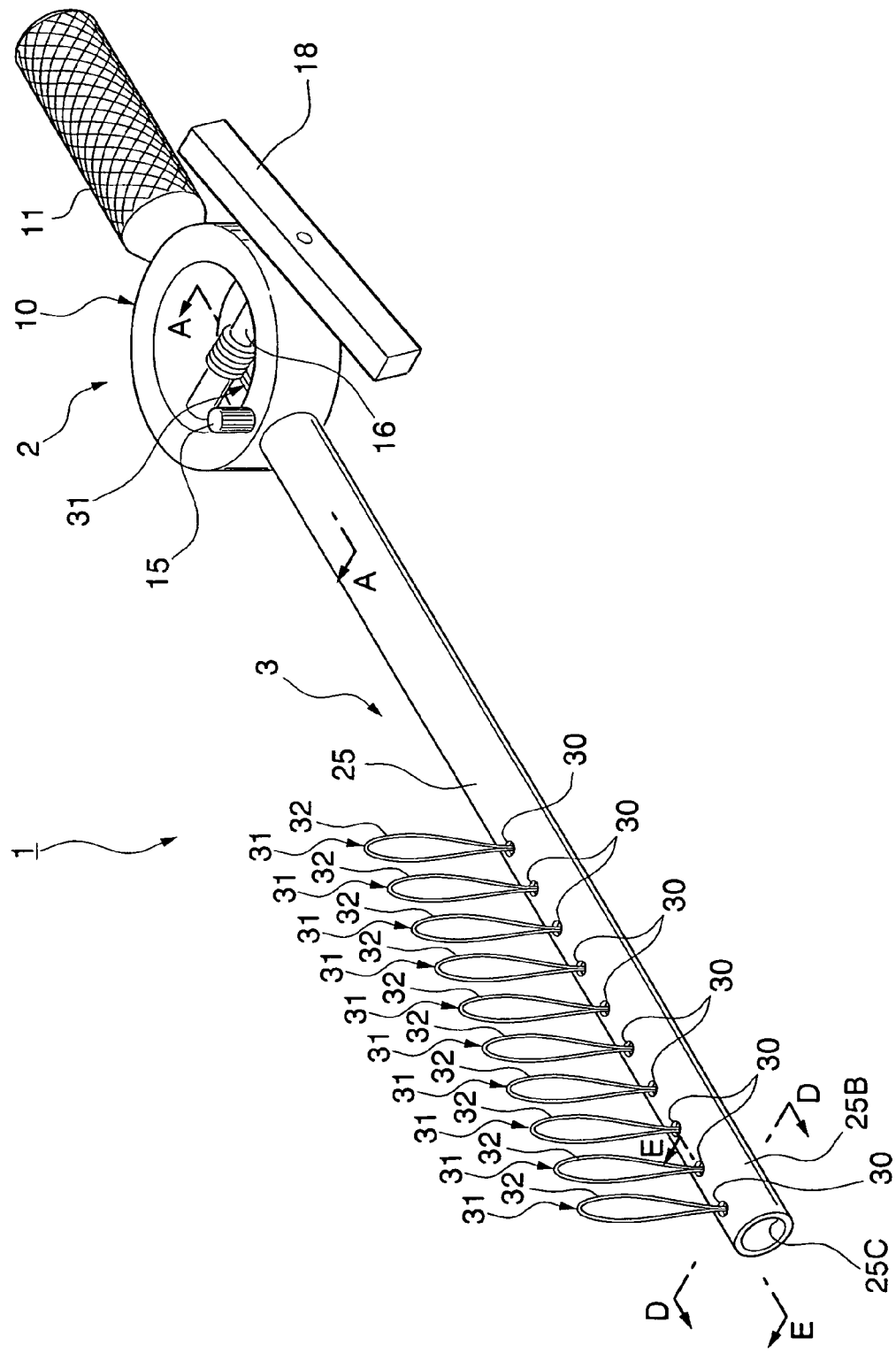
FIG. 1 is a view illustrating a configuration of a tissue cutting device according to a first embodiment.

Preferred embodiments will be explained. Like constituent parts in each embodiment are designated with like reference numerals, and are not repetitiously explained.

FIRST EMBODIMENT

Figure 2:
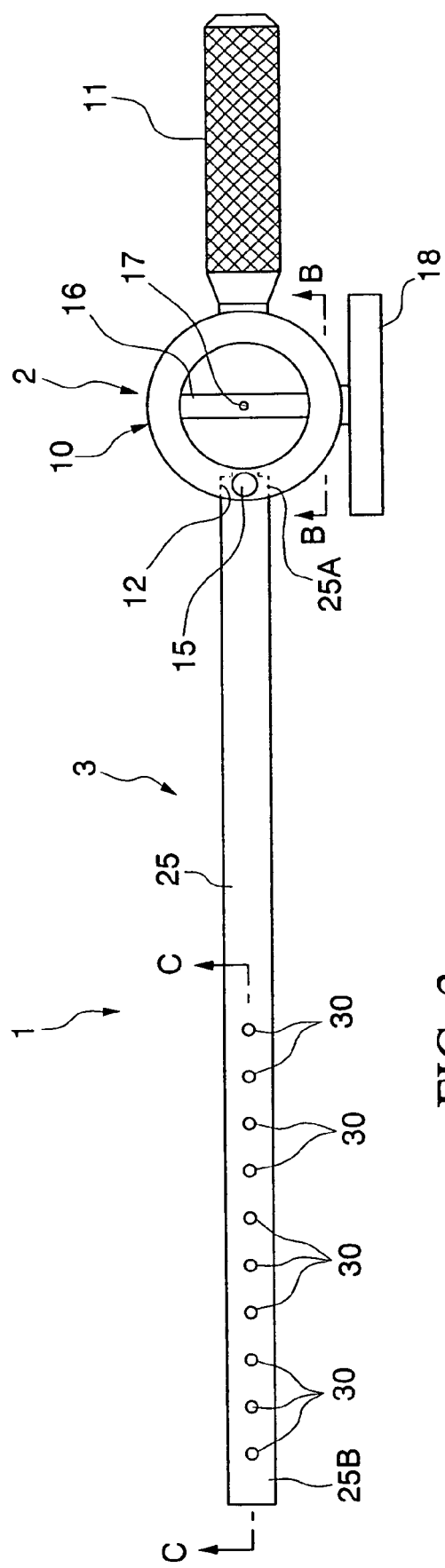
FIG. 2 is a plan view illustrating the tissue cutting device of FIG. 1.

In FIGS. 1 and 2, a tissue cutting device 1 includes a controller 2 which is controlled outside the body by an operator, and an insertion section 3 which extends from a distal end of the controller 2 and is inserted into an abdominal cavity.

Figure 3:
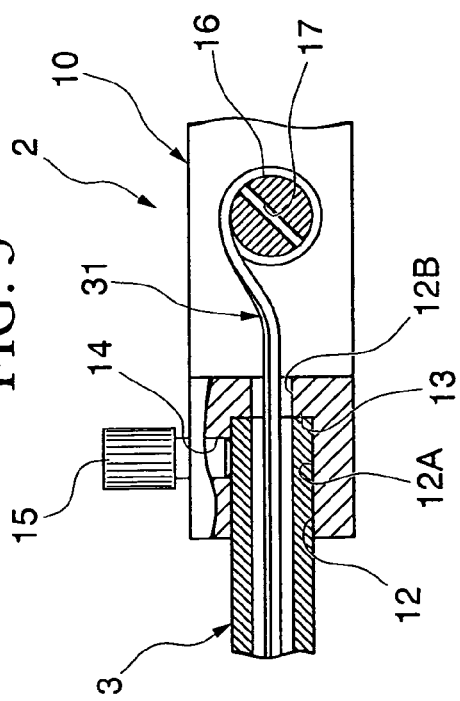
FIG. 3 is a cross-sectional view taken along line A-A of FIG. 1.

The controller 2 includes a ring-shaped control main unit 10, and a grip 11 which is secured at a predetermined position on the outer peripheral face of the control main unit 10. A through-hole 12 is formed penetrating from the outer peripheral face to an inner peripheral face at a position on the opposite side of the control main unit 10 in the peripheral direction with respect to the position where the grip is secured. As shown in FIG. 3, the diameter of the outer peripheral side of the through-hole 12 is sufficient to allow the insertion section 3 to be inserted therein. The diameter of the through-hole 12 is smaller at a proximal end side (inner peripheral side of the control main unit 10) than at a distal end side (outer peripheral side of the control main unit 10), and a proximal end of the insertion section 3 abuts against a step 13 formed between a large diameter portion 12A and a small diameter portion 12B. A screw hole 14 connecting to the large diameter portion 12A is provided in the control main unit 10, and is provided orthogonal to the axial line of the through-hole 12. The insertion section 3 can be secured to the control main unit 10 by screwing a screw 15 into the screw hole 14 such that it abuts to the outer periphery of the insertion section 3.

A shaft 16 functions as a control member, and is rotatably supported in the control main unit 10 such that it is provided orthogonal to the axial line which joins the grip 11 and the through-hole 12 (the axial line of the controller 2). A through-hole 17 is formed in the shaft 16 along the axial line of the controller 2.

Figure 4:
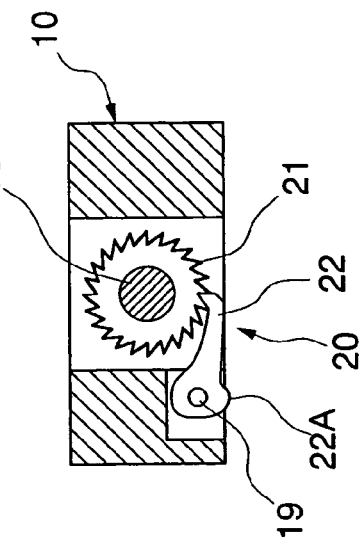
FIG. 4 is a cross-sectional view taken along line B-B of FIG. 2.

As shown in FIG. 2, one end of the shaft 16 extends from the outer peripheral face of the control main unit 10 and secured to a handle 18 which forms part of the controller 2. As shown in FIG. 4, a ratchet mechanism 20 can restrict the movement of the shaft 16 in the rotational direction. The ratchet mechanism 20 includes a ratchet toothed gear 21 secured to the shaft 16, and a ratchet claw 22 which is rotatably supported by a pin 19 on the control main unit 10 side. The ratchet claw 22 is urged by an unillustrated elastic member such that it engages with the ratchet toothed gear 21. A part 22A of the ratchet claw 22 is exposed to the outside from the control main unit 10. The engagement between the ratchet claw 22 and the ratchet toothed gear 21 can be removed by pressing this part 22A with a finger.

As shown in FIGS. 1, 2, and 5, the insertion section 3 includes an elongated pipe 25. A proximal end portion 25A of this pipe 25 is secured to the control main unit 10, and a plurality of openings 30 are provided in a row in the length direction on a distal end portion 25B side of the pipe 25. The openings 30 connect to a hole 25C which runs from the distal end portion 25B to the proximal end portion 25A. An axial line L1 which passes through a center of the opening 30 is approximately orthogonal to an axial line L2 of the pipe 25 and of the hole 25C. Similarly, an axial line passing through a center of each of the opening 30 along the insertion section 3 is approximately orthogonal to the axial line L2 extending from the distal end portion 25B of the insertion section 3 to the proximal end portion 25A. Tissue cutting members which are wires 31 (linear members) pass through each hole 30. A wire 31 extends outside the pipe 25 from one hole 30, and is led back into the pipe 25 from the same hole 30 after forming a loop in a direction approximately orthogonal to the axial line L2 of the pipe 25. The looped portion thus formed becomes a cutting section 32 which cuts tissue. One wire 31 forms a cutting section 32 from each hole 30. The cutting sections 32 are formed in the direction intersecting the axial line L2 of the pipe 25 (approximately orthogonally in this case). The size of each cutting section 32 (i.e. the size of the looped portion) is approximately the same for each wire 31. The ends of the wires 31 which lead through the openings 30 into the pipe 25 extend from the proximal end of the pipe 25.

The insertion section 3, and the control main unit 10, the grip 11, and the handle 18 of the controller 2 may be formed from insulating members. Instead of using insulating members, the surface of each member may be covered with an insulating material.

As shown in FIG. 3, the wires 31 pass through the small diameter portion 12B of the through-hole 12 in the control main unit 10 and are inserted through the through-hole 17 of the shaft 16. The ends of the wires 31 may pass only through the through-hole 17, or they may be secured to the shaft 16 by unillustrated interlocking members, or directly connected to the shaft 16.

Subsequently, the action of the tissue cutting device I will be explained. While the following explanation describes an example where an organ is completely removed during laparoscopic surgery, the target for cutting may be an organ such as a kidney or a liver, or tissue from part of an organ or another type of organ.

After insufflating the abdominal cavity of the patient, a puncture hole is made in the abdominal wall and a trocar is inserted. A laparoscope is inserted via the trocar into the abdominal cavity and a kidney is observed. A treatment instrument is inserted via a trocar through another puncture hole. After carrying out procedures on blood vessels and the like of the kidney, the kidney is isolated using the treatment instrument. The treatment instrument is then removed from the abdominal cavity and a forceps is inserted in its place. An insertion section of a tissue cutting device is inserted into the abdominal cavity via a trocar through yet another puncture hole.

When inserting the tissue cutting device 1 into a body cavity, the looped cutting portions 32 are wound tightly around the pipe 25 to reduce their diameters. The outer diameters of the cutting sections 32 may be reduced by pressing them along the axial line of the insertion section 3.

Figure 6:
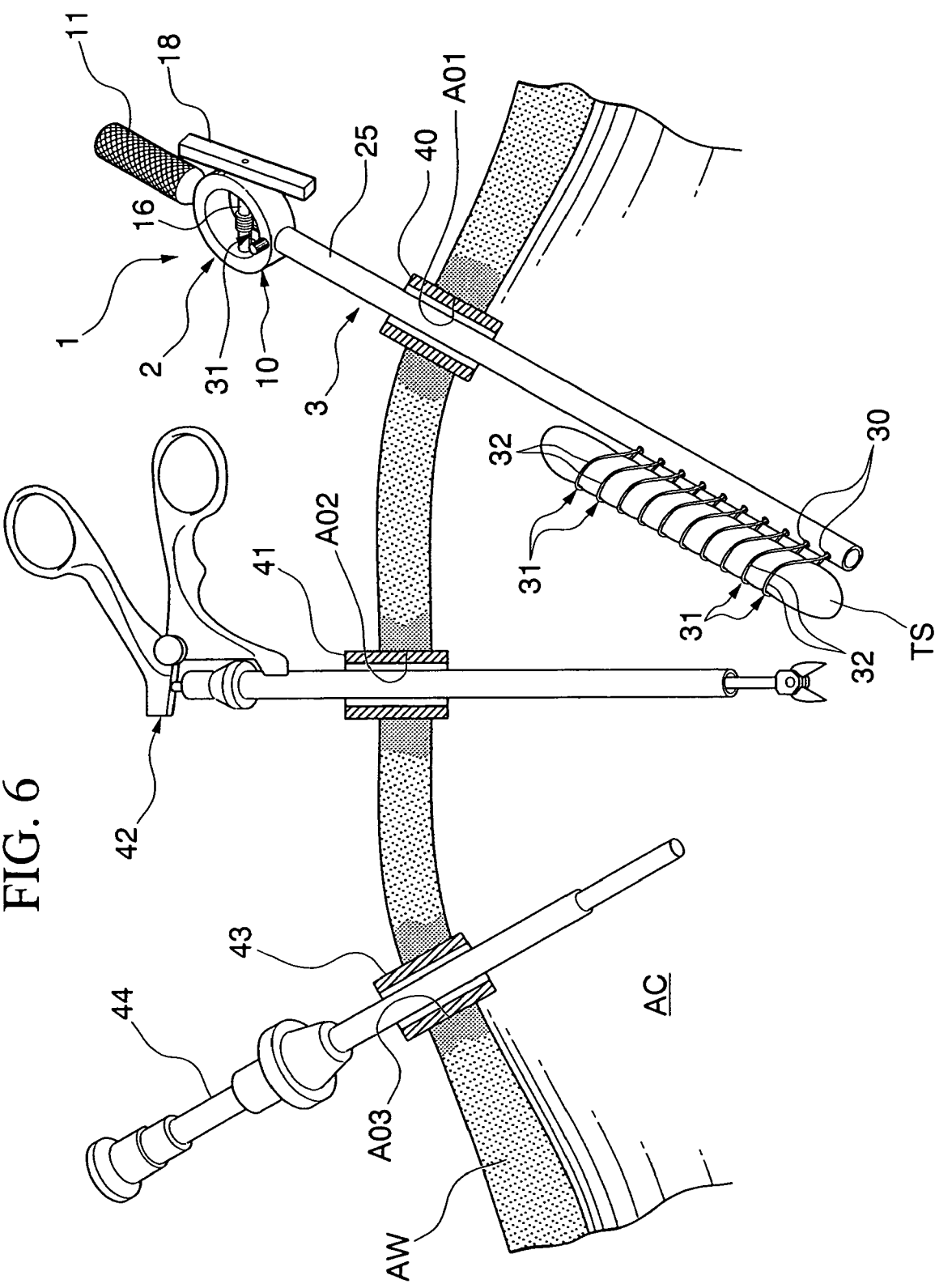
FIG. 6 is a view illustrating a procedure for cutting a tissue.

When the tissue cutting device 1 is inserted into the abdominal cavity via the trocar, the elastic force of the cutting sections 32 returns them to their original shapes. Alternatively, a forceps may be used to return the cutting sections 32 to their original shapes. As shown in FIG. 6, a forceps 42 is passed through a trocar 41 and cuts an organ TS which is then inserted into the cutting sections 32. This procedure is performed while monitoring it with a laparoscope 44 inserted through a trocar 43.

Figure 7:
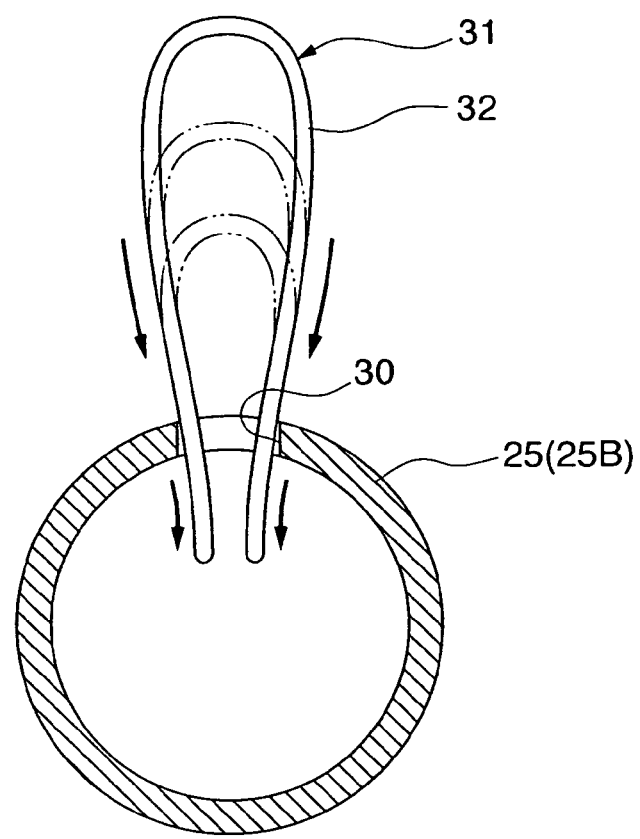
FIG. 7 is a cross-sectional view taken along line D-D of FIG. 1, illustrating a step of gradually drawing in a wire.
Figure 8:
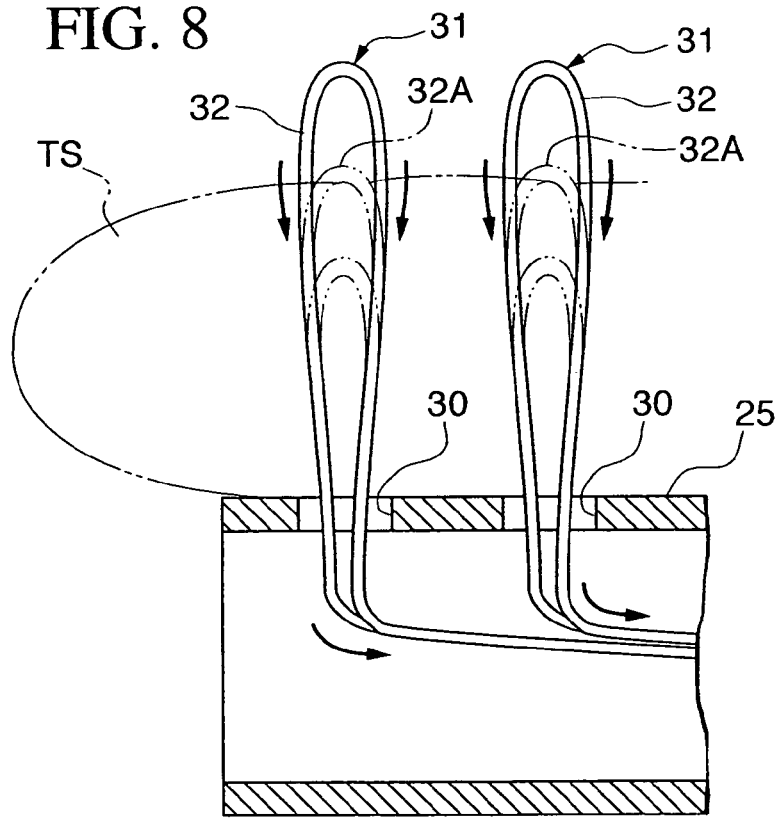
FIG. 8 is a cross-sectional view taken along line E-E of FIG. 1, illustrating a step of gradually drawing in a wire.

When the organ TS is accommodated in the cutting sections 32, the handle 18 of the controller 2 is rotated. The rotation of the handle 18 rotates the shaft 16, winding the ends of the wires 31 around it. Since the ratchet mechanism 20 prevents the handle 18 from rotating in the opposite direction, rotating the handle 18 while gripping it gradually pulls the wires 31 towards the hand side. As shown in FIGS. 7 and 8, the wires 31 forming the looped cutting portions 32 which extend from the openings 30 of the pipe 25 are gradually drawn through the openings 30 into the pipe 25 such that an entirely of each tissue cutting member is retracted inside the insertion section. As a result, the diameters of the cutting sections 32 are reduced (the lengths of the circular arc of the loops decrease), and, in the manner of the cutting sections 32A indicated by the imaginary lines of the example in FIG. 8, they abut to and press against the outer periphery of the organ TS accommodated inside the loops.

When the handle 18 is rotated further in the same direction, the cutting sections 32 are drawn further into the openings 30 of the pipe 25 such that their outer diameters (circular arc lengths) become smaller than the outer periphery of the organ TS, whereby the cutting sections 32 cut the organ TS. The timing of the cutting of the organ TS or the like differs according to the hardness of the tissue, the ease of contraction, and so on. Moreover, the timing of the contact between the cutting sections 32 and the tissue differs according to the shape of the tissue. Consequently, the timings of cutting the tissue differ according to the positions where the wires 31 are provided. Nevertheless, since each wire 31 is ultimately drawn completely inside the pipe 25 via one opening 30, the tissue is cut by the cutting sections 32 of the wires 31 no later than before the wires 31 are drawn completely inside the pipe 25.

As shown in FIG. 6, small pieces of the cut organ TS are extracted outside the body one by one using the forceps 42. When all the small pieces of the cut organ TS are extracted, the tissue cutting device 1, the forceps 42, and the laparoscope 44 are removed from the abdominal wall AW, the trocars 40, 41, and 43 are removed, and the puncture holes AO1, AO2, and AO3 are closed.

According to this embodiment, in minutely cutting the organ TS inside the abdominal cavity AC and removing it to outside the body, each wire 31 extending in a loop from one opening 30 cuts the organ TS, thereby enabling the wires 31 to be drawn completely into the pipe 25. Therefore, the organ TS can be cut reliably. Conventionally, since wires are inserted sequentially via two openings in a head main unit to form a loop, a gap is liable to form between the head main unit and the extracted wire between the openings, making it impossible to completely cut the organ. To make it easier to cut the organ, it is conventional to receive the wires in grooves such that the peripheral edges of the grooves and the wires tear away the organ. However, it is difficult to actually reduce the gap between the head main unit and the wires to zero (airtight state) while the tissue is sandwiched between the head main unit and the wires by providing grooves. It is also difficult to receive the wires in the grooves while sandwiching the organ, and, if the widths of the grooves are reduced in order to receive the wires more easily, it becomes difficult to tear away the organ. This embodiment can solve these problems and cut the organ more reliably.

Furthermore, since the openings 30 are formed in a row along the length direction of the pipe 25 and a loop of the wire 31 (cutting section 32) is formed in each of the openings 30, the organ TS can be cut into a plurality of small pieces and removed easily. In particular, since the organ TS can be removed without large cutting of the abdominal wall AW, increase in the invasion for the patient can be prevented. Since the wires 31 are drawn completely into the pipe 25 at this time, the fine pieces of the cut organ TS can easily be grasped and extracted using the forceps 42 or the like.

Since the wires 31 are wound by rotating the handle 18, the organ TS can be cut easily using a small amount of force. Conventional configurations, in which a wire is pulled linearly, require a large force and a long stroke. In this embodiment, the controller 2 can be made compact.

Figure 9:
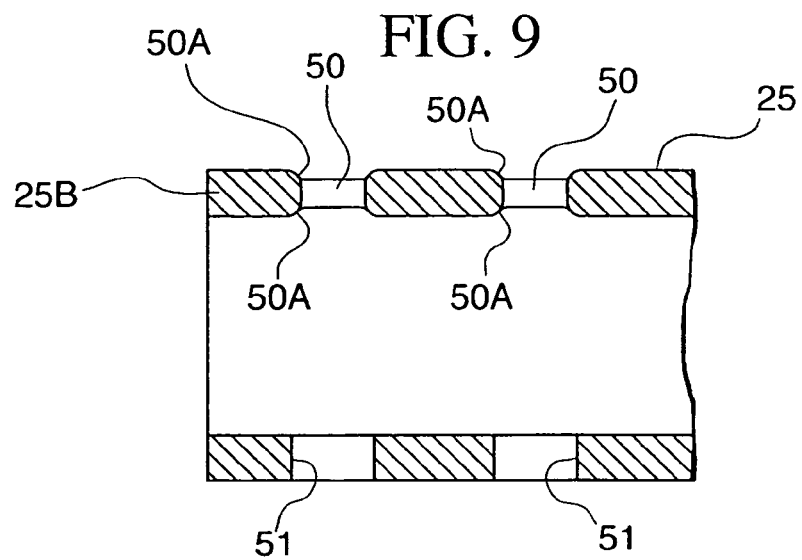
FIG. 9 is a cross-sectional view illustrating a modification in which curved-surface processing is performed to ends of openings.

As shown by openings 50 in FIG. 9, curved-surface processing may be performed such that the diameter of each opening end 50A increases smoothly; in other words, the open ends of the openings are chamfered such that the diameters of the openings expand. Using such openings 50 reduces resistance when the wires 31 are drawn in from them, enabling the organ to be cut with a small amount of force.

Holes 51 provided opposite the openings 50 are used for inserting tools such as tools for curved-surface processing.

SECOND EMBODIMENT

Figure 10:
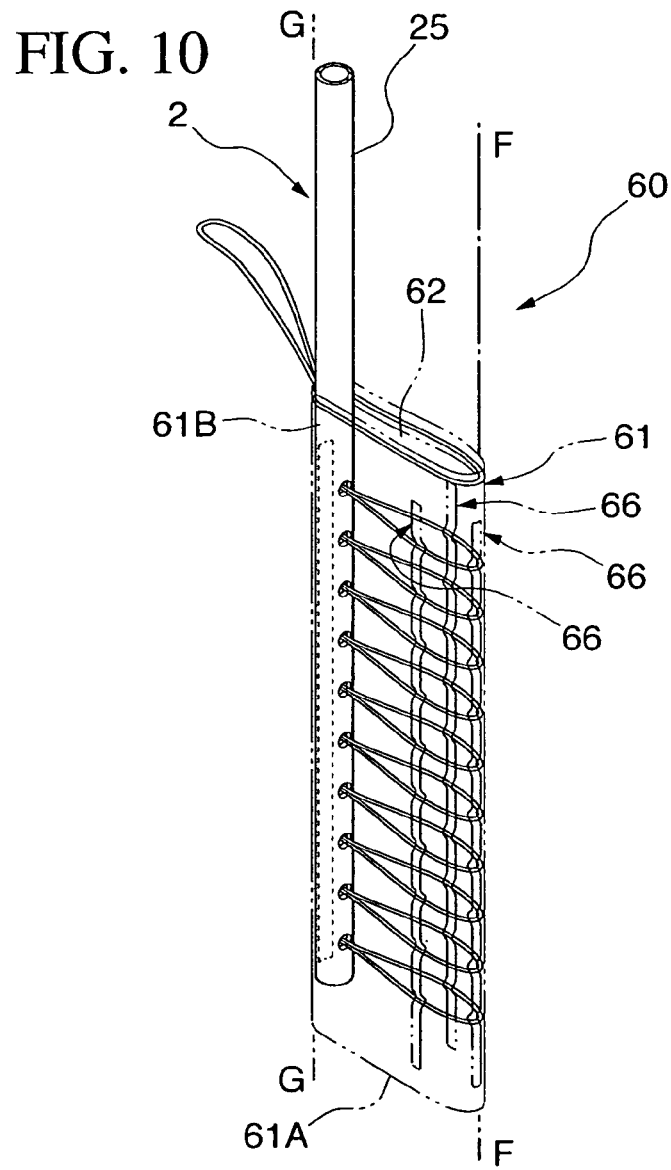
FIG. 10 is a view illustrating a configuration of a tissue cutting device according to a second embodiment.
Figure 11:
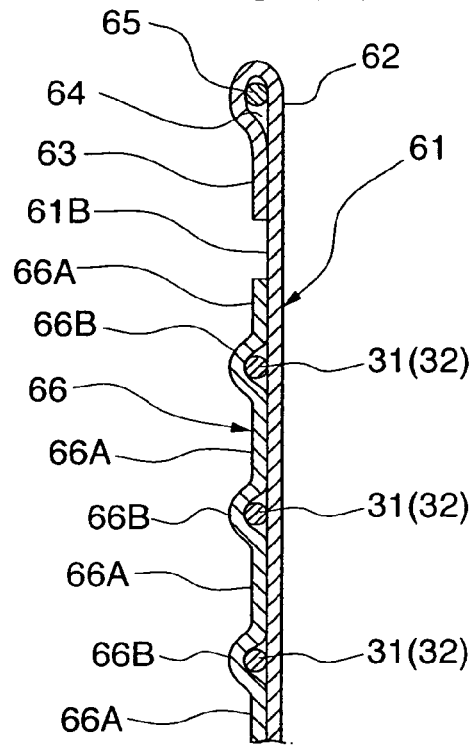
FIG. 11 is a cross-sectional view taken along line F-F of FIG. 10.

FIG. 10 shows a tissue cutting device 60 according to a second embodiment. In the tissue cutting device 60, the distal end section of the pipe 25 of the insertion section 3 where the openings 30 are formed is inserted into a bag unit 61. An inner peripheral face of the bag unit 61 is attached to a side of the pipe 25 on a side opposite to that of the openings 30. A distal end 61A side of the bag unit 61 is sealed, and a proximal end 61B side has an opening 62. As shown in FIG. 11, a peripheral edge 63 of the opening 62 is bent and thermally attached to form a passage 64, which a cord 65 is inserted through.

Figure 12:
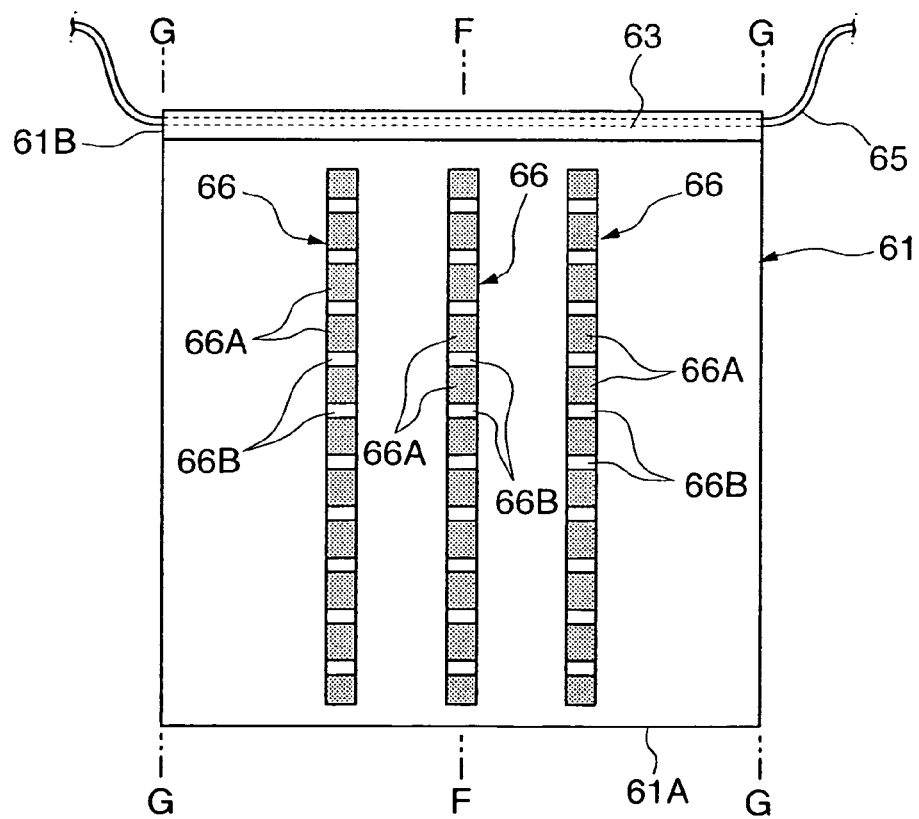
FIG. 12 is a view illustrating a bag unit exploded along line G-G of FIG. 10.

As shown in FIGS. 11 and 12, a plurality of band members 66 are secured in parallel to the inner side of the bag unit 61 in a predetermined length direction. The band members 66 are thermally attached to the bag unit 61 at predetermined intervals in the length direction, and one wire 31 passes through each nonattached section 66B between attached sections 66A. While in FIG. 12 three band members 66 are attached, one, two, four, or more, may be attached instead. A controller of this tissue cutting device 60 has the same configuration as in the first embodiment.

When cutting an organ TS, the wires 31 and the bag unit 61 are wound along the outer periphery of the pipe 25 during insertion into the abdominal cavity AC.

After insertion into the abdominal cavity AC, the elastic force of the cutting sections 32 returns them to their original shapes. A forceps or the like may be used to return the cutting sections 32 and the bag unit 61 to their original shapes and make an opening 62 in the bag unit 61. The organ TS is inserted into the bag unit 61. Since the plurality of wires 31 pass through the nonattached sections 66B of the band members 66 and extend approximately along the inner peripheral face of the bag unit 61, when the organ TS is inserted into the bag unit 61, the organ TS is accommodated in the cutting sections 32 of the wires 31.

A forceps or the like is used to pull the cord 65 and close the opening 62 of the bag unit 61. The handle 18 of the controller 2 is then rotated in the same manner as the first embodiment, pulling the wires 31. This severs the nonattached sections 66B, allowing the wires 31 to be drawn through their respective openings 30 and into the pipe 25. As the size of the cutting sections 32 decreases, the organ TS is cut into a plurality of pieces. Closing the opening 62 of the bag unit 61 before cutting the organ TS prevents the tissue and the like of the organ TS from spattering and sticking to other organs and the like.

After cutting the organ TS, the tissue cutting device 60 is removed to outside the body with the small pieces of the organ TS accommodated in the bag unit 61. In the case of a large organ TS, the tissue cutting device 60 is extracted together with the entire organ TS after removing the trocar. In the case of an even larger organ TS, only the opening 62 of the bag unit 61 is removed outside the body and opened; the cut pieces of the organ TS are then extracted one by one using a forceps or the like.

In this embodiment, the bag unit 61 can prevent the tissue of the cut organ TS from spattering. For example, if the organ TS contains a lesion such as cancerous cells, the lesion can be prevented from sticking to other organs and metastasizing the cancerous cells to them. Since the band members 66 can be used to form the cutting sections 32 of the wires 31 along the bag unit 61, the organ TS can easily be accommodated in the plurality of cutting sections 32. Moreover, since the organ TS remains in the bag unit 61 after cutting, it can easily be removed outside the body.

THIRD EMBODIMENT

Figure 13:
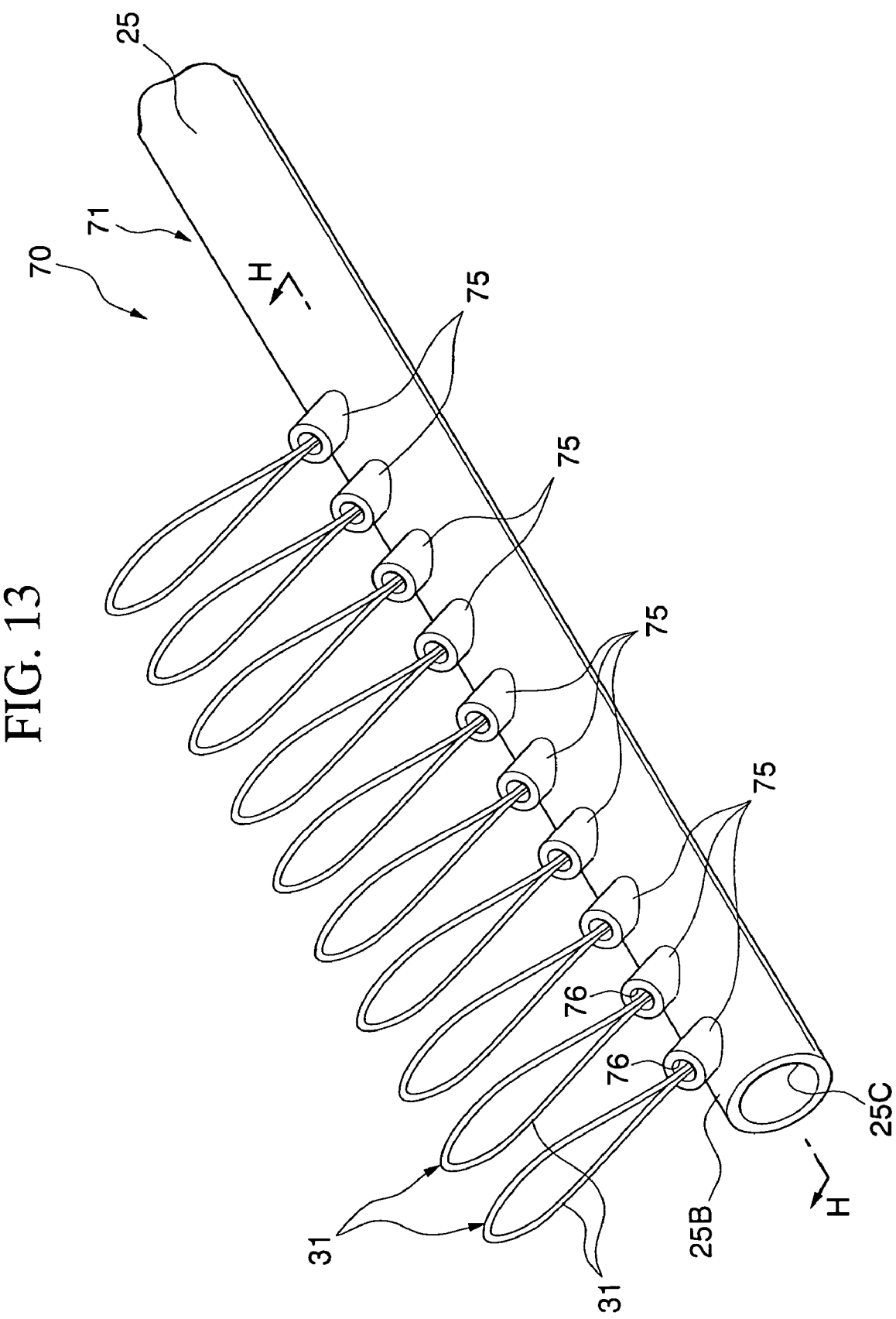
FIG. 13 is a view illustrating a configuration of a tissue cutting device according to a third embodiment.
Figure 14:
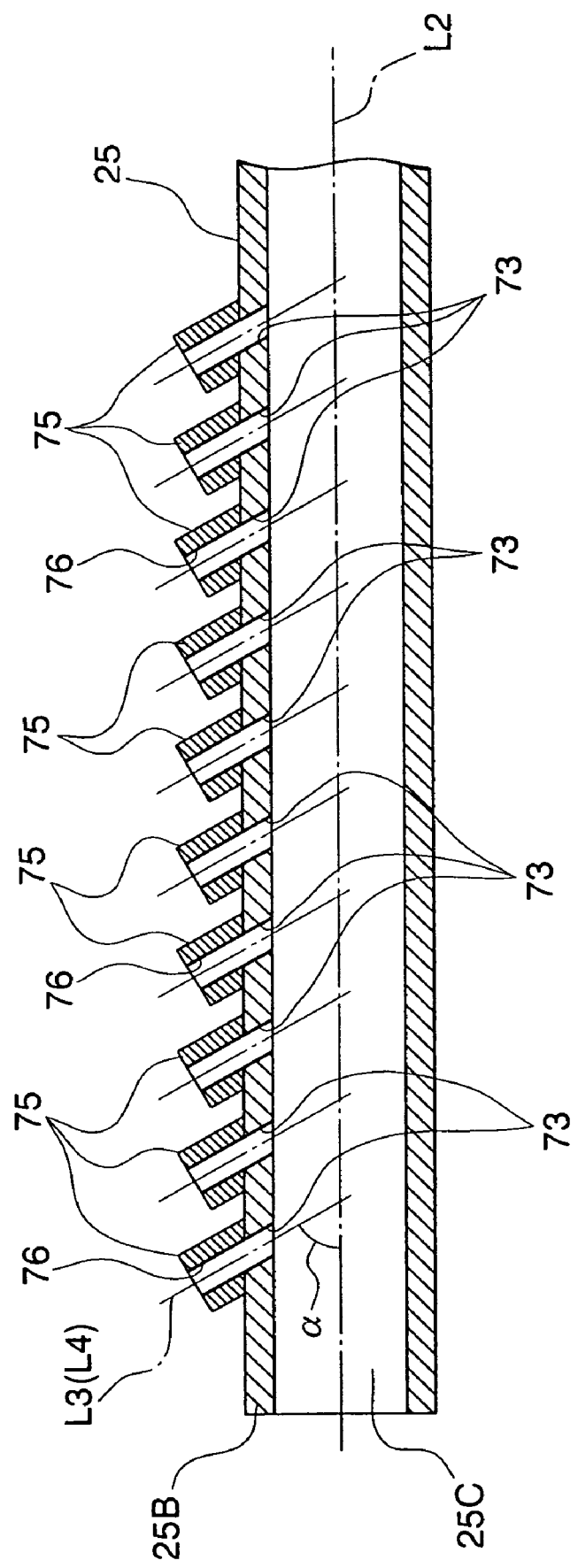
FIG. 14 is a cross-sectional view taken along line H-H of FIG. 13.

A tissue cutting device 70 shown in FIGS. 13 and 14 includes an insertion section 71 which is inserted into an abdominal cavity AC. The insertion section 71 includes a cylindrical pipe 25, and a plurality of openings 73 which are formed in a row along the length direction of the pipe 25. Each opening 73 slopes towards the distal end of the insertion direction such that it faces more toward this distal end than a direction approximately orthogonal to the central axis (axial line L2) of the pipe 25, thereby forming an acute angle α between an axial line L3 of the opening 73 and the axial line L2 of the pipe 25. Hollow end members 75 (branch sections) are securely attached around the outer periphery of the pipe 25 and connect to the opening 73. Each end member 75 has one through-hole 76, and an axial line L4 of the through-hole 76 approximately matches the axial line L2 of the opening 73. A wire 31 passes through one opening 73 and along the inside of the end member 75 connected to that opening 73, and extends to the outside. The wire 31 then passes again through the same end member 75 and the opening 73 and leads back into the pipe 25, forming a looped cutting portion 32 which intersects the axial line L2 of the pipe 25 (at a gradient angle α).

When cutting the organ TS, the organ TS is passed inside the cutting sections 32. When the wires 31 are pulled by rotating the handle 18, the wires 31 forming the cutting sections 32 pass through the through-holes 76 in the end members 75 and are drawn through the openings 73 into the pipe 25. At this time, since an acute angle is formed between the line segment which extends from the axial line L2 of the pipe 25 to the openings 73 and the direction which the wires 31 are pulled in, there is small frictional drag when the wires 31 are pulled through the openings 73 to the proximal end side of the pipe 25. Consequently, the wires 31 can be drawn smoothly.

In this embodiment, since the cutting sections 32 of the wires 31 extend from the pipe 25 at a diagonal (intersecting direction) to the distal end and the sides, frictional drag in the vicinity of the openings 73 when pulling the wires 31 can be reduced. This enables the organ TS to be cut with less force. The load on the wires 31 can be reduced, and their diameters can be made narrower. Since the cut face of the tissue is cleaner in this case, the capability for pathological diagnosis is increased. By attaching the end members 75 to the pipe 25, even if the openings 73 of the pipe 25 have a short length, the wires 31 can easily be extracted in the desired direction.

FOURTH EMBODIMENT

Figure 15:
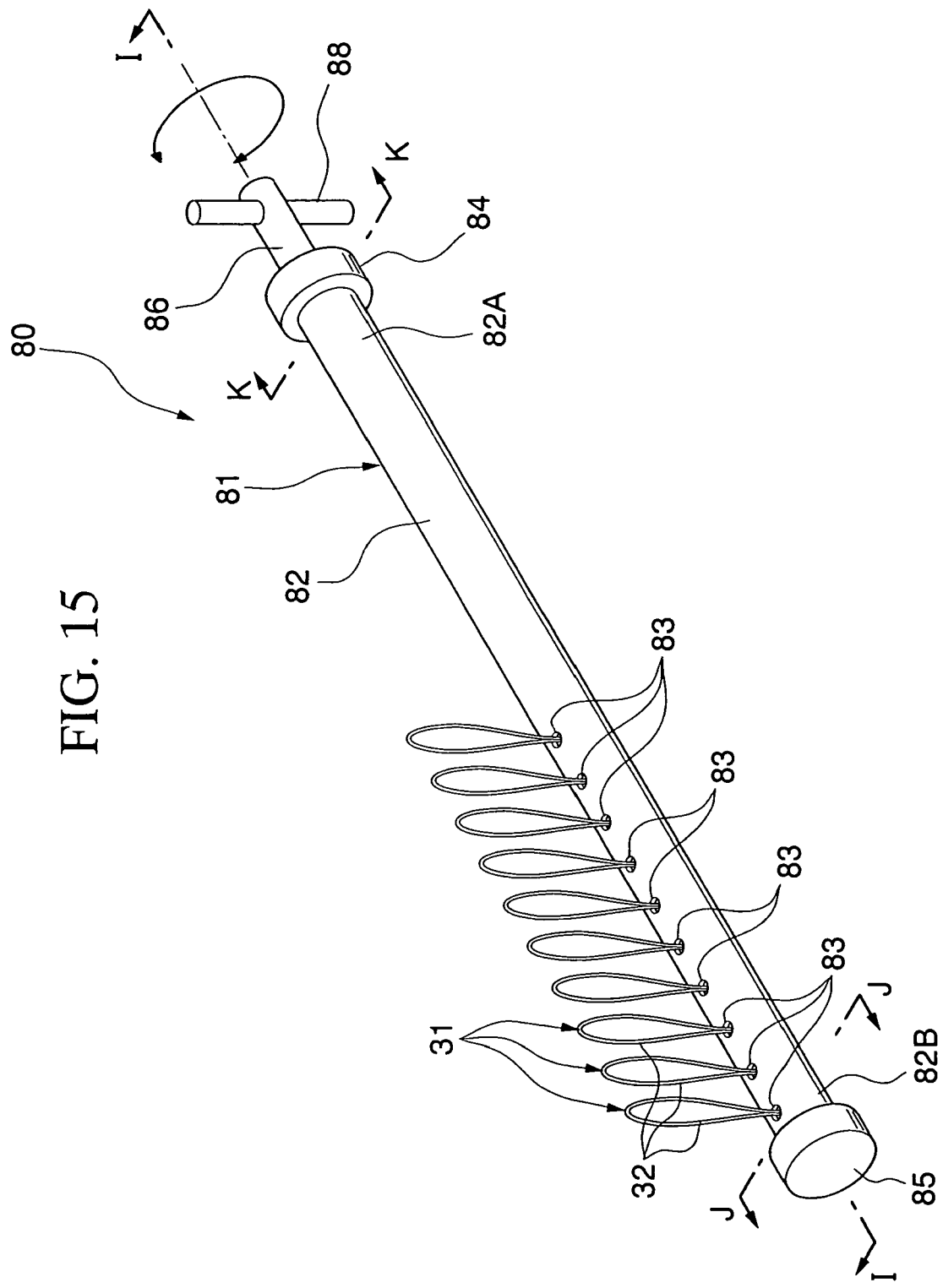
FIG. 15 is a view illustrating a configuration of a tissue cutting device according to a fourth embodiment.
Figure 16:
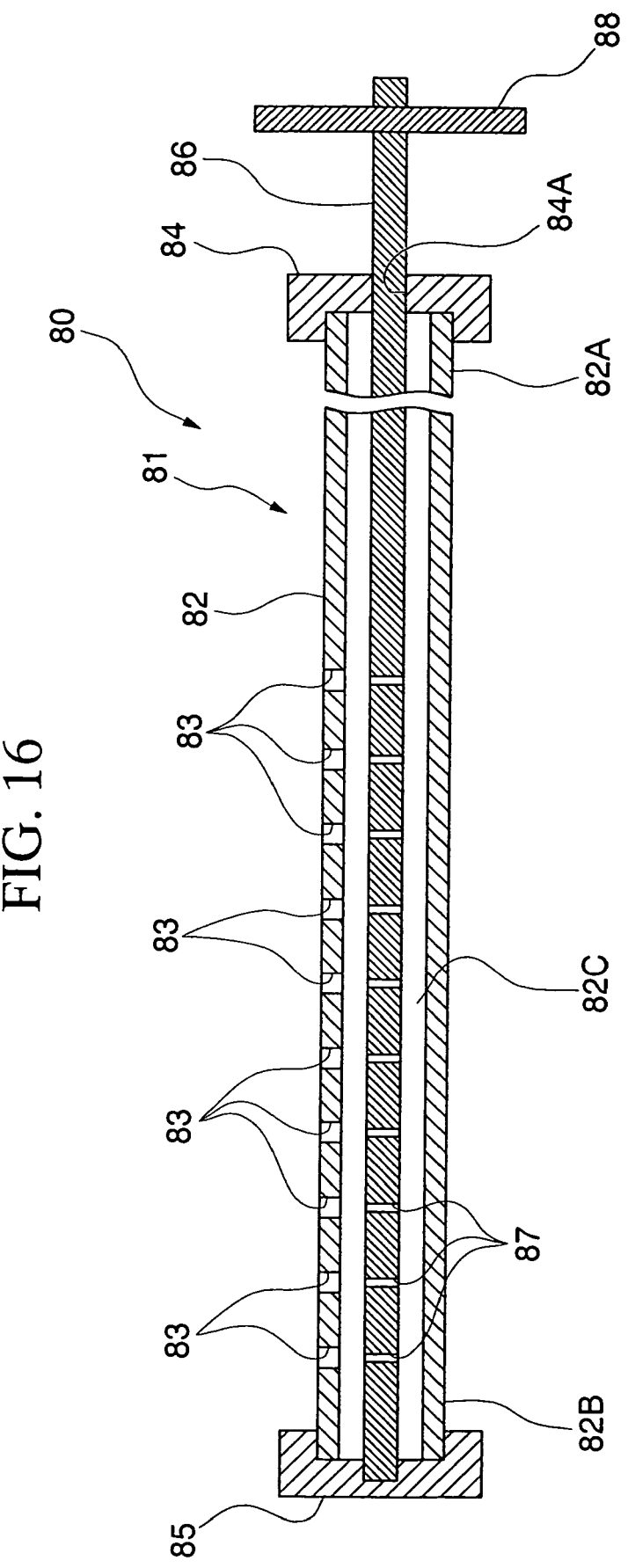
FIG. 16 is a cross-sectional view taken along line I-I of FIG. 15.

In FIGS. 15 and 16, a tissue cutting device 80 includes an elongated insertion section 81. The insertion section 81 includes a hollow pipe 82. A row of openings 83 are provided at predetermined intervals in the length direction of the pipe 82 from its distal end side. Securing members 84 and 85 are secured respectively at ends 82A and 82B of the length direction of the pipe 82. A through-hole 84A is formed in the center of the securing member 84 at the proximal end side, and a control member made from a shaft 86 is inserted through this through-hole 84A. The shaft 86 is arranged coaxially on the axial line of the hollow pipe 82, and a plurality of through-holes 87 are provided at predetermined intervals along its length direction from its distal end. The positions of the through-holes 87 match those of the openings 83 on the pipe 82 side. The axial line of the through-holes 87 and the axial line of the openings 83 on the pipe 82 side are approximately orthogonal to the axial line of a hole 82C in the pipe 82. A handle 88 forming a control section is inserted into the proximal end of the shaft 86 such that it is orthogonal to the axial line of the shaft 86.

Each wire 31 is extends from one opening 83 to the outside of the pipe 82, where it forms a looped cutting portion 32; the wire 31 is then drawn through the same opening 83 back into the pipe 82 and secured inside the through-hole 87 of the shaft 86. The looped cutting portions 32 intersect (in this case, approximately orthogonally) with the axial line of the pipe 82.

Figure 17:
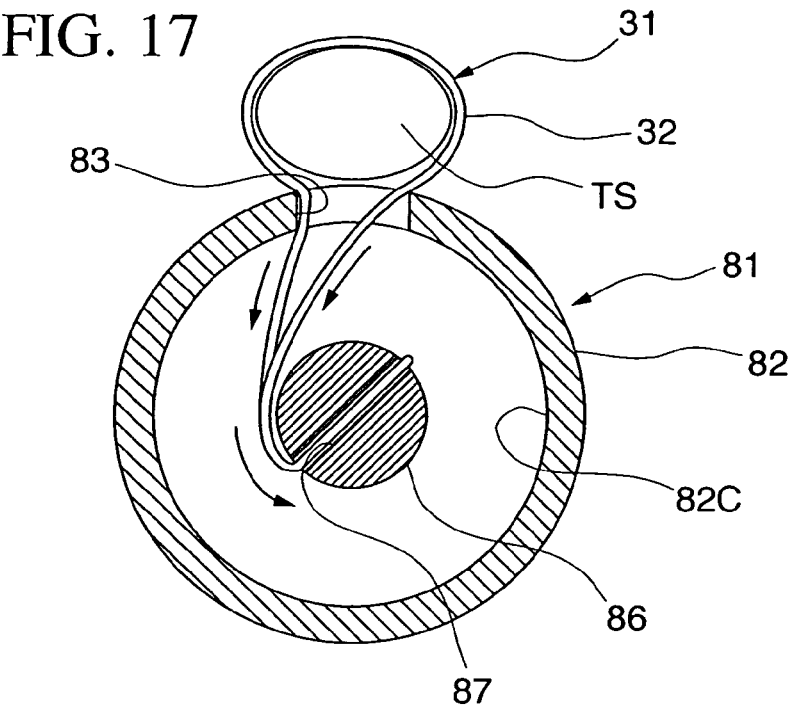
FIG. 17 is a cross-sectional view taken along line J-J of FIG. 15, illustrating how a wire is wound about a shaft.

When cutting an organ TS accommodated in the cutting sections 32 of the wires 31, the handle 88 at the proximal end of the shaft 86 is rotated. As shown in FIG. 17, the wires 31 are wound around the outer periphery of the shaft 86, and the looped cutting portions 32 protruding from the pipe 82 are gradually drawn through the openings 83 into the pipe 82. This reduces the size of the cutting sections 32 and cuts the organ TS.

In this embodiment, the provision of the shaft 86 which winds the wires 31 enables the organ TS to be cut by rotation by hand. Since it is easy for an operator to apply a force to the handle 88 and wind the wires 31 about the shaft 86, the organ TS can be cut with a small force.

A modification of this embodiment will be explained.

Figure 18:
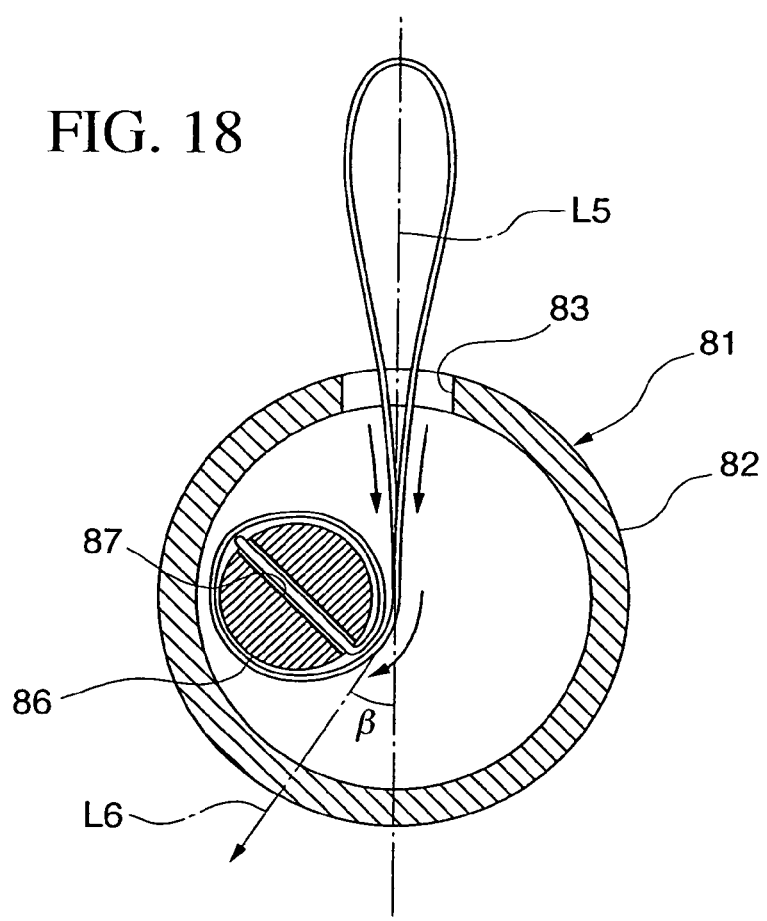
FIG. 18 is a cross-sectional view taken along line J-J of FIG. 15, illustrating a modification in which a shaft is offset.
Figure 19:
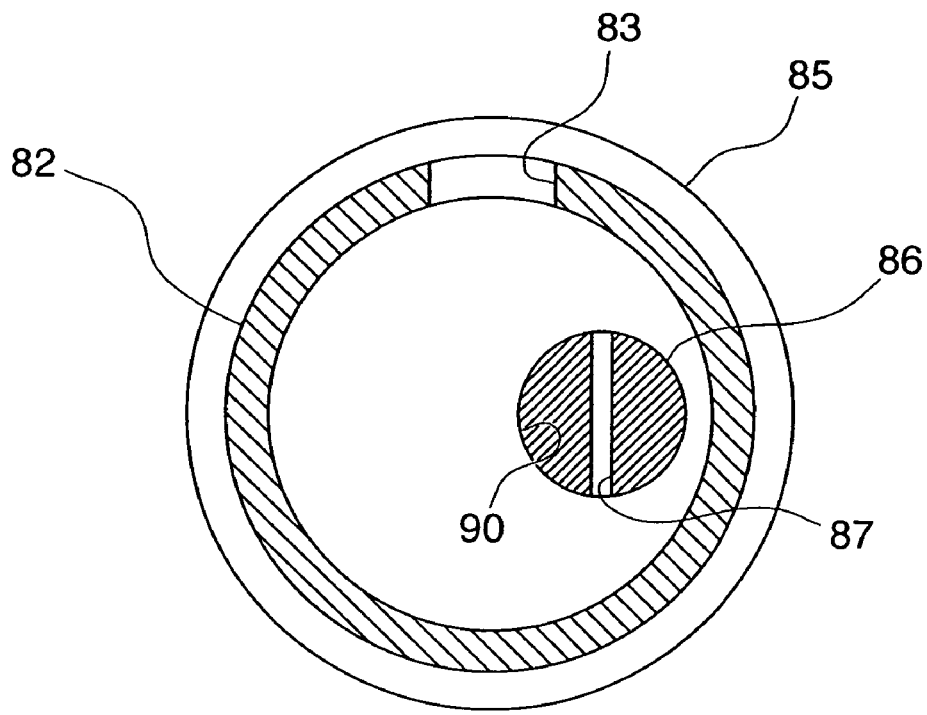
FIG. 19 is a cross-sectional view taken along line J-J of FIG. 15, illustrating the shape of the shape of a securing member at a distal end side when the shaft is offset.
Figure 20:
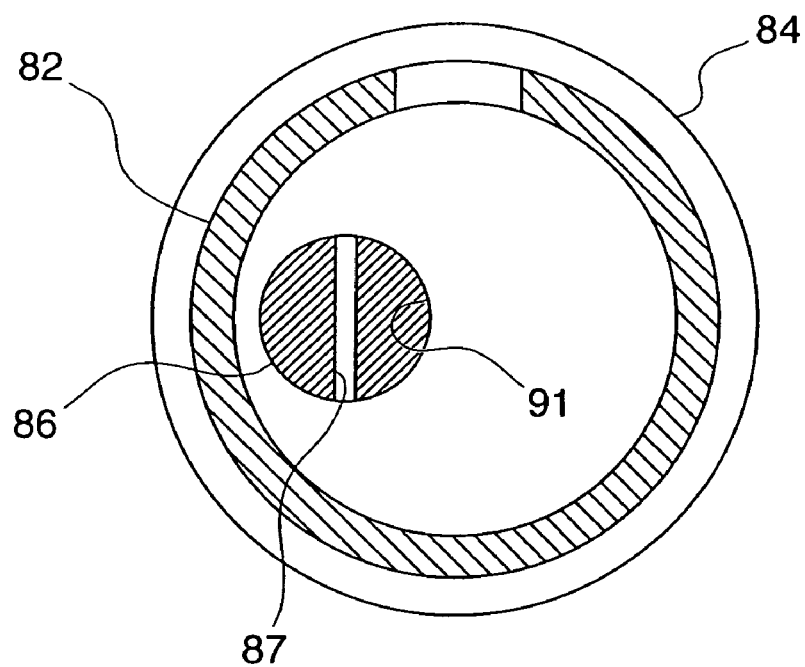
FIG. 20 is a cross-sectional view taken along line K-K of FIG. 15, illustrating the shape of the shape of a securing member at a proximal end side when the shaft is offset.

As shown in FIG. 18, the outer peripheral face of the shaft 86 may be offset such that it does not intersect with an axial line L5 of the opening 83. As shown in FIG. 19, the securing member 84 which rotatably supports the shaft 86 includes a concave 90 offset from the center, and the distal end of the shaft 86 is rotatably fitted into this concave 90. As shown in FIG. 20, a through-hole 91 is also provided in the securing member 84 and is offset in the same direction from the center. The shaft 86 is rotatably inserted through this through-hole 91.

When cutting an organ TS accommodated in the cutting sections 32 of the wires 31, the handle 88 at the proximal end side of the shaft 86 isrotated. The rotation direction is one which achieves an acute angle β between the direction of drawing the wires 31 into the openings 83 and the tangential line L6 of the direction of winding the wires 31 about the shaft 86; in the example of FIG. 18, this is the clockwise direction. When the shaft 86 is rotated in this direction, the wires 31 drawn inside from the openings 83 are wound around the outer periphery of the shaft 86 without greatly changing their direction of movement, enabling the organ TS to be cut by winding the wires 31 with a small force.

In this modification, in addition to the effects mentioned above, since the shaft 86 is offset with respect to the axial line of the pipe 82, the resistance when drawing the wires 31 into the openings 83 can be reduced and the organ TS can be cut with an even smaller force.

FIFTH EMBODIMENT

Figure 21:
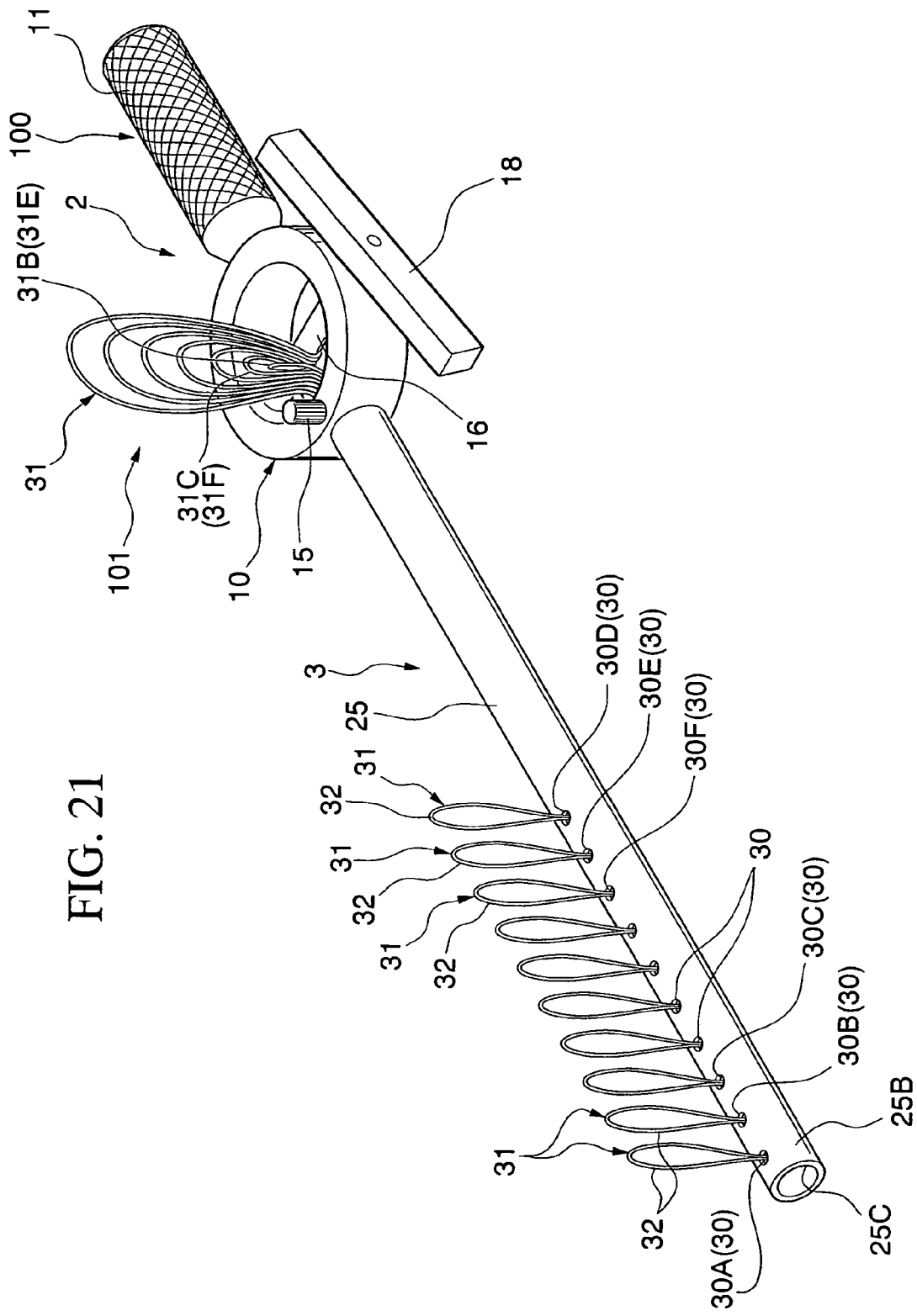
FIG. 21 is a view illustrating a configuration of a tissue cutting device according to a fifth embodiment.

In a tissue cutting device 100 shown in FIG. 21, a timing adjustment portion 101 is formed by loosening the wires 31 between the proximal end of a pipe 25 of an insertion section 3 and a shaft 16. The amount of loosening the wires 31 decreases as they approach the openings 30 at both ends of the length direction of the pipe 25. That is, the wire 31 which passes through the opening 30A nearest the distal end of the pipe 25 is secured to the shaft 16 with almost no loosening, while the wire 31 which passes through an opening 30B second from the distal end is secured to the shaft 16 after being given a short loose section 31 B. The wire 31 which passes through an opening 30C third from the distal end is secured to the shaft 16 after being given a loose section 31C which is larger than that of the second wire 31. The wire 31 which passes through an opening 30D nearest from the proximal end is secured to the shaft 16 with almost no loosening, while the wire 31 which passes through an opening 30E second from the proximal end is secured to the shaft 16 after being given a short loose section 31E. The wire 31 which passes through an opening 30F third from the proximal end is secured to the shaft 16 after being given a loose section 31F which is larger than that of the second wire 31. The wire 31 which passes through the opening 30 in the center of the length direction has the largest loose section.

When cutting the organ TS accommodated in the cutting sections 32 of the wires 31, the handle 18 of the controller 2 is rotated. As the shaft 16 rotates, the wires 31 are wound around it. Since the wires 31 which pass through the openings 30A and 30D at the ends (first wires 31) are not loosened, they immediately start to be drawn in from the openings 30A and 30D, cutting the organ TS. The wires 31 which pass through the openings 30B and 30E second from the ends start to be drawn in from the openings 30B and 30E after their loose sections 31B and 31E have been wound about the shaft 16, and start cutting the organ TS at a timing later than that of the first wires 31 by an amount equivalent to the length of the loose sections 31B and 31E. Thereafter, the wires 31 are drawn from the openings 30 in sequence according to the lengths of the loose sections forming the timing adjustment portion 101, whereby they sequentially cut the organ TS from both ends at time differences which correspond to the lengths of their loose sections. As a result, the organ TS can be cut with a smaller force than when all the wires 31 are drawn in from the openings 30 simultaneously.

If the wire 31 corresponding to the opening 31A at the distal end of the pipe 25 is loosened the least, and the amount of loosening for the subsequent wires 31 is increased sequentially toward the proximal end, the organ TS can be cut sequentially from the distal end side.

While the lengths of the loose sections can be set as desired, the amount of force can be further reduced by setting the amount of loosening such that, for example, after the first wire 31 is completely drawn inside the opening 30A, the adjacent wire 31 (second wire 31) starts to be drawn into the opening 30B. If the setting is such that, when the first wire 31 starts to cut the organ TS, the adjacent second wire 31 directly contacts the outer periphery of the organ TS, the second wire 31 can secure the organ TS in position while the first wire 31 is cutting and can prevent the organ TS from deviating from its position. Therefore, the organ TS can be reliably cut in a desired position. Moreover, the amounts of loosening may be set such that the wire 31 nearest the proximal end is the first to be drawn in, or set individually such that the wires 31 are drawn in according to any given sequence.

The timing adjustment portion 101 may be configured by gradually changing the outer diameter of the shaft 16 in the length direction. Since the wires 31 wound around the large diameter portion of the shaft 16 are wound by a large amount when the shaft 16 is rotated once, they are drawn in quickly. Since the wires 31 wound around the small diameter portion of the shaft 16 are wound by a small amount when the shaft 16 is rotated once, they are drawn in slowly. By changing the outer diameter of the shaft 16 in this way, the timings can be altered. The timings can also be altered by changing the outer diameter of the shaft 86 in the second embodiment to form a timing adjustment portion.

SIXTH EMBODIMENT

Figure 22:
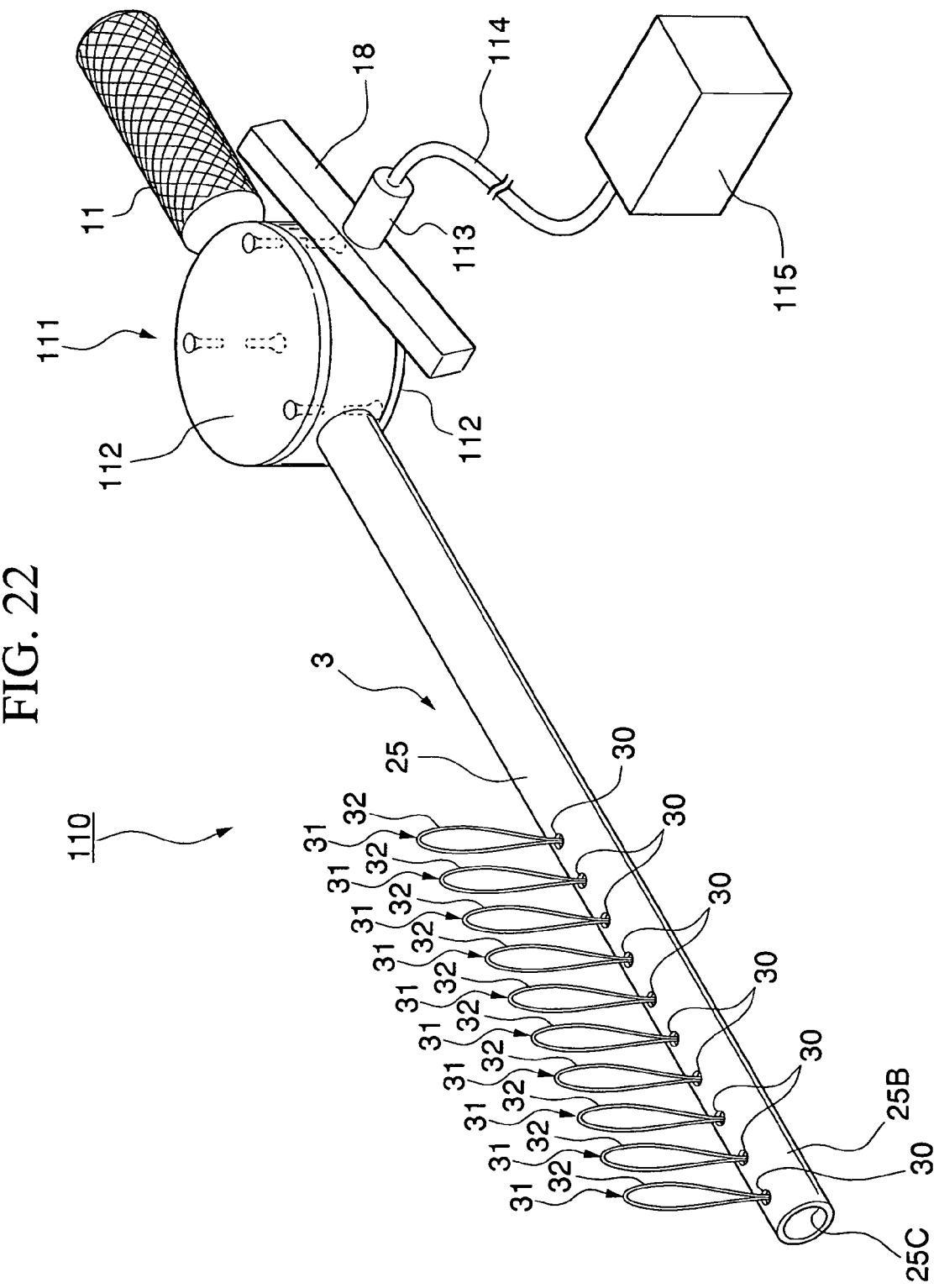
FIG. 22 is a view illustrating a configuration of a tissue cutting device according to a sixth embodiment.

This embodiment relates to a tissue cutting device for high-frequency cutting. In FIG. 22, a tissue cutting device 110 includes wires 31 made from conductive members. The shaft 16 is also made from a conductive member, and is electrically connected to a high-frequency power source 115 via a cord 114 which is inserted from a connector 113 provided as an extension to the handle 18. The handle 18, the control main unit 10, the grip 11, and the pipe 25 is made of insulated members. An insulating lid 112 is secured by screws to the control main unit 10 such that it seals the opening in the control main unit 10.

In this tissue cutting device 110, when the organ TS is passed into the cutting sections 32 and the handle 18 is rotated, the cutting sections 32 tighten around the organ TS. An electrical current is applied from the high-frequency power source 115 and burns off the organ TS. By cutting the organ TS in this manner, it can be cut reliably without requiring a large force.

Figure 23:
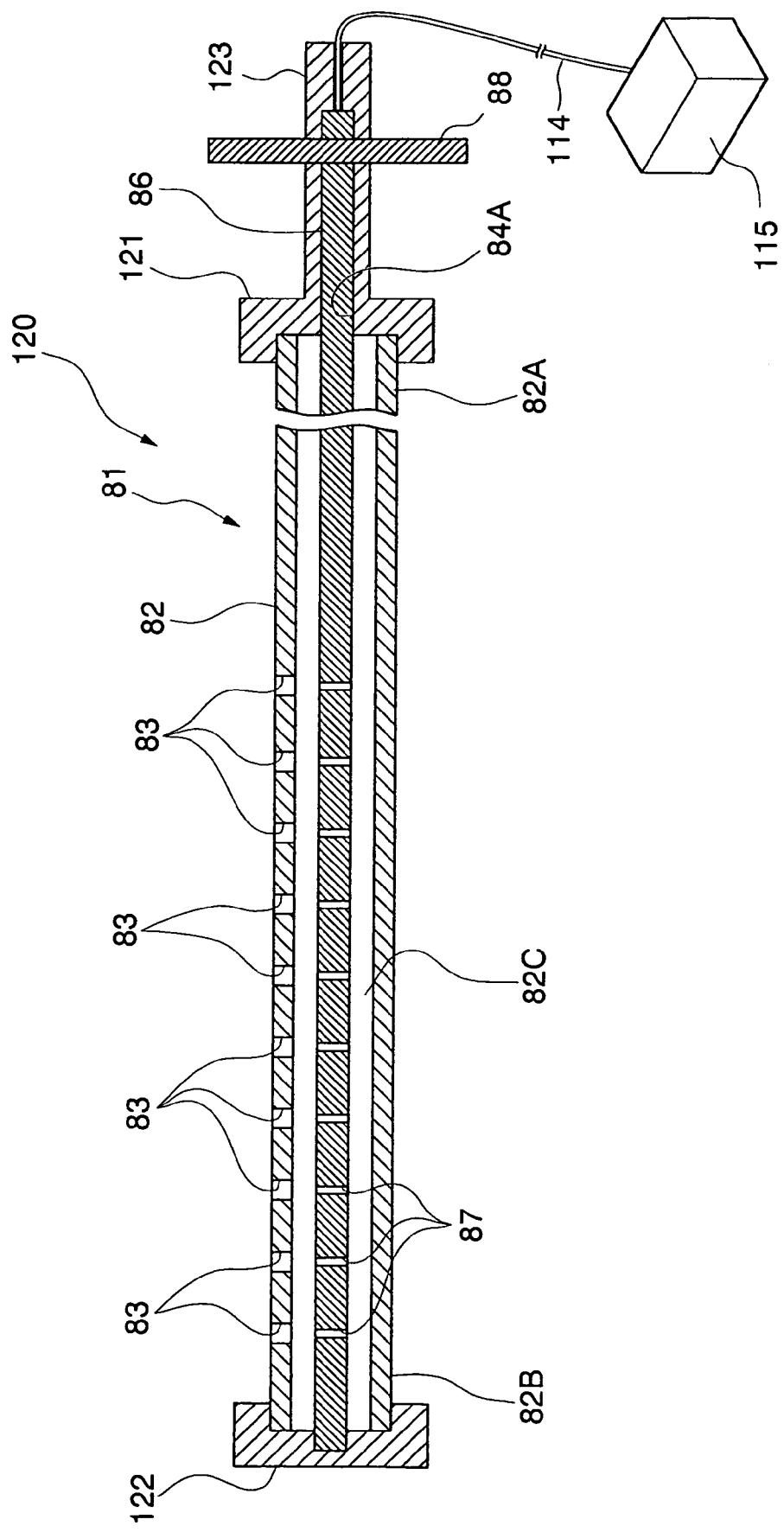
FIG. 23 is a view illustrating a configuration of a tissue cutting device according to the sixth embodiment.

In FIG. 23, a tissue cutting device 120 includes wires 31 and a shaft 86 which are made from conductive members. Securing members 121 and 122 and the handle 88 are made from insulated members. A proximal end of the securing member 121 forms a connector 123 which extends along the axial direction of the pipe 82. The connector 123 covers the outer periphery of the shaft 86, and the handle 88 extends from an opening formed in a side section thereof. The cord 114 extends from the proximal end section of the connector 123 and connects to the shaft 86. The cord 114 electrically connects the wires 31 to the high-frequency power source 115.

When cutting the organ TS, the organ TS is passed inside the cutting sections 32 and the handle 88 is rotated. The securing member 121 and the shaft 86 rotate with respect to the pipe 82, winding the wires 31 about the shaft 86 and tightening the cutting sections 32 around the organ TS. An electrical current is then applied from the high-frequency power source 115 and burns off the organ TS. By cutting the organ TS in this manner, it can be cut reliably without requiring a large force.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

For example, the insertion section is not limited to a cylindrical shape and may instead comprise a plate member. In this case, a plurality of openings are provided at predetermined intervals along the length direction of the plate member. Wires aligned with one face of the plate member are passed through the openings, and extend in a direction intersecting with the length direction of the plate member on the other face side of the plate member to form loops. It is also acceptable to provide slits in the plate member and use these slits as openings for passing the wires through.

The number of openings is not limited to those in the embodiments, and one opening would be acceptable.

The controller 2 may draw the cutting sections 32 into the openings (e.g. openings 30) by pulling the wires 31 in a straight line.

The tissue cutting members may comprise closed loops formed by linear members. In this case, some of the closed loops extends from one opening (e.g. opening 30) and the remaining loops are wound about the shaft 16 (86) and cut the organ TS. Alternatively, a linear control member may be provided together with, or secured to, the closed loops, enabling the loops to be drawn in through one opening (e.g. opening 30) by pulling the linear control member, thereby cutting the organ TS.

What is claimed is:

1. A tissue cutting device comprising:
   an insertion section which is inserted inside a specimen and extends from a distal end to a proximal end;
   openings which are formed in a row along an outer peripheral face of a distal end side of the insertion section inserted into the specimen, wherein the row extends from the distal end towards the proximal end;
   tissue cutting members, each of the tissue cutting members passing through a respective one of the openings, each of the tissue cutting members extending such as to protrude in a direction intersecting, at an angle, an axial line of a length direction, the axial line extending from the distal end of the insertion section to the proximal end, and each of the tissue cutting members being drawn into the insertion section from the respective one of the openings after forming loops which tissue can be inserted into, each loop being formed by a single one of the tissue cutting members;
   a control member which is connected to the tissue cutting members; and
   a controller for controlling the control member;
   wherein each of the tissue cutting members is protruded from and drawn into the insertion section through a same one of the openings, and wherein tissue passed into the loops is cut by controlling the control member and drawing the tissue cutting members from the openings completely into the insertion section such that an entirety of each of the tissue cutting members is retracted inside the insertion section.

2. The tissue cutting device according to claim 1, wherein the control member includes a shaft which is inserted into the insertion section and is rotatably supported by the insertion section around an axial line of the length direction, the controller being used to rotate the shaft such that the tissue cutting members are wound around the outer periphery of the shaft and the tissue cutting members are drawn from the openings into the insertion section.

3. The tissue cutting device according to claim 2, wherein the axial line of the shaft is offset with respect to the axial line of the length direction of the insertion section.

4. The tissue cutting device according to claim 1, further comprising
   a bag unit which surrounds the tissue cutting members extending from the insertion section, the bag unit being sealed at a distal end thereof and open at a proximal end thereof.

5. The tissue cutting device according to claim 1, wherein the control member pulls the tissue cutting members which pass through the insertion section to the proximal end of the insertion section.

6. The tissue cutting device according to claim 5, wherein the controller draws the tissue cutting members from the openings into the insertion section by rotating the control member and winding the tissue cutting members around the control member.

7. The tissue cutting device according to claim 1, wherein the openings slope toward the distal end side of the insertion section such as to form an acute angle with the axial direction of the insertion section.

8. The tissue cutting device according to claim 7, further comprising
   branch sections which through-holes facing in approximately a same direction as the openings are formed in, the branch sections being secured to the insertion section such that the through-holes and the openings communicate.

9. The tissue cutting device according to claim 1, further comprising
   a timing adjustment portion which varies the timings of drawing the tissue cutting members from the openings into the insertion section.

10. The tissue cutting device according to claim 9, wherein the timing adjustment portion is formed by varying lengths of the tissue cutting members between the proximal end of the insertion section and the control member according to positions of the openings.

11. The tissue cutting device according to claim 9, wherein the timing adjustment portion is configured such that after drawing one tissue cutting member in from a corresponding opening, another tissue cutting member which is adjacent to that tissue cutting member is drawn in through a corresponding opening.

12. The tissue cutting device according to claim 9, wherein the timing adjustment portion is configured such that before drawing one tissue cutting member in through a corresponding opening, another tissue cutting member which is adjacent to that tissue cutting member starts to be drawn in through a corresponding opening.

13. The tissue cutting device according to claim 1, wherein end regions of the openings on and near an outer surface and on and near an inner surface of the insertion section are chamfered such that diameters of the openings expand.

14. The tissue cutting device according to claim 1, wherein the tissue cutting members are made of conductive members, and are configured such that an electrical current can be applied to.

15. The tissue cutting device according to claim 2, further comprising
   a timing adjustment portion which varies timings of drawing the tissue cutting members from the openings into the insertion section.

16. The tissue cutting device according to claim 15, wherein
   the timing adjustment portion is configured such as to vary a diameter of the shaft which the tissue cutting members are wound around.

17. The tissue cutting device according to claim 1, wherein axial lines which pass through centers of the openings are approximately orthogonal to the axial line extending from the distal end of the insertion section to the proximal end.

* * * * *